United States Patent

Duffill et al.

[11] Patent Number: 6,105,431
[45] Date of Patent: Aug. 22, 2000

[54] ULTRASONIC INSPECTION

[75] Inventors: Colin Duffill, Oxford; Maurice Geoffrey Silk, Abingdon, both of United Kingdom

[73] Assignee: Aea Technology PLC, Didcot, United Kingdom

[21] Appl. No.: 08/945,852

[22] PCT Filed: May 7, 1996

[86] PCT No.: PCT/GB96/01078

§ 371 Date: Nov. 7, 1997

§ 102(e) Date: Nov. 7, 1997

[87] PCT Pub. No.: WO96/36874

PCT Pub. Date: Nov. 21, 1996

[30] Foreign Application Priority Data

May 18, 1995 [GB] United Kingdom ............... 9510032

[51] Int. Cl.$^7$ .................................................. G01N 29/04
[52] U.S. Cl. ................................ 73/624; 73/629; 73/596
[58] Field of Search .......................... 73/596, 597, 598, 73/599, 600, 618, 620, 624, 627, 628, 629

[56] References Cited

U.S. PATENT DOCUMENTS

| | | | |
|---|---|---|---|
| 3,646,805 | 3/1972 | Walters | 73/625 |
| 3,712,119 | 1/1973 | Cross et al. | 73/614 |
| 4,052,889 | 10/1977 | Mucciardi et al. | 73/629 |
| 4,165,649 | 8/1979 | Greer, Jr. | 73/644 |
| 4,570,487 | 2/1986 | Gruber | 73/624 |
| 5,115,414 | 5/1992 | Atalar et al. | 367/7 |
| 5,431,054 | 7/1995 | Reeves | 73/612 |

*Primary Examiner*—Richard A. Moller
*Attorney, Agent, or Firm*—William H. Holt

[57] ABSTRACT

A plate (12) or pipe wall is inspected by coupling an ultrasonic transducer (14, 16) to its surface so as to generate a compression wave or lateral wave (26) along the surface and a shear wave or head wave (28) along the surface and a shear wave or head wave (28) at the shear-compression critical angle ($\theta_c$) The same transducer (14, 16), or an additional transducer (15, 16) also coupled to the surface, detects a series of ultrasonic peaks corresponding to each generated ultrasonic pulse. Each such detected peak corresponds to ultrasonic energy traveling, partly as lateral waves (26, 32) on one surface or the other, and partly as head waves (28, 30) crossing a certain number of times between the surfaces. The transducers (14, 15) may be over 0.5 m apart, and substantially all the intervening parts of the plate (12) are inspected.

7 Claims, 2 Drawing Sheets

ULTRASONIC INSPECTION

This invention relates to a method and to an apparatus for inspecting an object such as a wall or plate using ultrasonic waves, more particularly using lateral waves.

By lateral waves are meant compression waves propagating close to a surface of an object; such waves may also be referred to as longitudinal surface waves or longitudinal subsurface waves. A lateral wave alone does not satisfy the boundary conditions at a stress-free surface, and so it continually generates a shear wave propagating into the bulk of the object, which may be referred to as a head wave. The lateral wave is thus attenuated. The properties of lateral waves have been studied for example by L. V. Basatskaya et al (Sov. J. NDT 16(7) July 1980) and by L. V. Yuozonene (Sov. J. NDT 16(8) August 1980). Basatskaya et al report that their analysis confirms previous experimental observations that lateral waves have little sensitivity to surface defects, whereas Yuozouene suggests lateral waves may be used to examine surface layers for surface defects. In a wall or plate with two opposed surfaces the head wave will generate another lateral wave at the opposite surface, so that lateral waves propagate along each surface.

According to the present invention there is provided a method for inspecting an object with two opposed substantially parallel major surfaces, the method comprising coupling a transmitter ultrasonic transducer to one of the major surfaces of the object so as to generate shear waves in the object propagating in a direction inclined from the normal to the surface at an angle substantially equal to the shear-compression critical angle; coupling a receiver ultrasonic transducer to one of the major surfaces of the object so as to detect shear waves incident at an angle of incidence equal to the shear-compression critical angle; energising the transmitter transducer to generate at least one pulse of ultrasound; and detecting by means of the receiver transducer a series of ultrasonic peaks corresponding to each generated pulse, the series of peaks being due to ultrasonic waves which have propagated through the object partly as lateral waves on the major surfaces and partly as head waves traversing the object between the major surfaces.

The receiver ultrasonic transducer may be the same transducer as is used to generate the ultrasonic waves, for example where the waves are reflected back to the transducer by an edge surface of the object or by a crack, flaw or defect on either surface or within the object. Alternatively, or additionally the transmitter transducer and the receiver transducer may be separate transducers, which are spaced apart from each other; they may be coupled to the same or to opposite major surfaces.

In general whenever a shear wave is incident at a boundary between media of differing elastic properties it is reflected as both a compression wave and a shear wave. The shear-compression critical angle is the angle of incidence for a shear wave for which the reflected compression wave is at 90° to the normal; if a shear wave is incident at an angle greater than this critical angle only shear waves are reflected. If the speed of compression waves is $C_p$ and the speed of shear waves is $C_s$ then the shear-compression critical angle $\theta_c$ is given by:

$$\theta_c = \sin^{-1}(C_s/C_p)$$

The transmitter and the receiver transducers may be more than 0.25 m apart, and may be as much as 1.0 m apart or more. The object may be a plate or wall, for example of a tank or a pipe, and might be for example between 5 and 25 mm thick. Substantially the entire volume of the object between the transducers is inspected, as lateral waves propagate along both the surfaces, and head waves (which propagate across to the opposite surface) are generated at all parts of a surface along which lateral waves are propagating. The exact nature of the received signals depends upon the thickness of the object, and on the material of which it is made, as well as being affected by the presence of any defects. The lateral wave can be expected to travel at substantially the same speed as a bulk compression wave, which for most materials is about twice that of shear waves. Hence after generation of a pulse, the first received peak at the same surface corresponds to propagation as a lateral wave the whole way; a later received peak corresponds to propagation as a lateral wave the whole way apart from two crossings of the object as a head wave; another corresponds to propagation as a lateral wave apart from four crossings of the object as a head wave; the next to propagation as a lateral wave apart from six such crossings; and so on. As long as the thickness of the object between the opposed major surfaces is uniform, the locations where such crossings take place are immaterial as the time of receipt is the same for all propagation paths which involve the same number of such crossings.

The received series of peaks may be analysed to provide information about the thickness of the object, or about any localised corrosion which locally changes the thickness. It can also be analysed to detect any defects, flaws or cracks in the object which reflect or obstruct the propagating waves. Information may also be obtained by examination of any signals received between successive peaks.

The invention will now be further and more particularly described, by way of example only, and with reference to the accompanying drawings in which.

Figure 1:
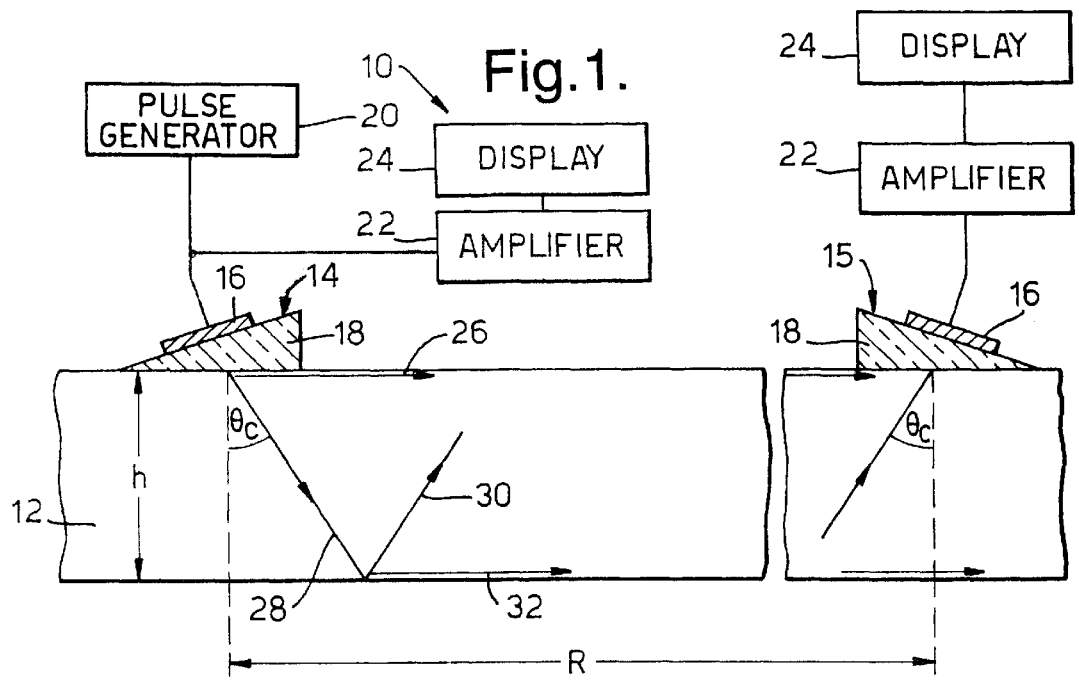
FIG. 1 shows a diagrammatic sectional view of an apparatus for ultrasonic inspection of a steel plate.

Referring to FIG. 1, an apparatus 10 is shown in use for inspection of a steel plate 12 which is 15 mm thick. The apparatus 10 comprises a transmitter 14 and a receiver 15 separated by a distance of 260 mm along the plate 12, each consisting of a piezo-electric transducer 16 for generating or receiving pulses of compression waves which is coupled to the plate 12 by a coupling prism 18 of polymethylmethacrylate. The angle of each prism 18 is such that plane compression waves propagating from the transducer 16 would be incident at the boundary between the prism 18 and the plate 12 at an angle $\theta_1$ given by:

$$\theta_1 = \sin^{-1}(C_c/C_p)$$

where $C_c$ and $C_p$ are the speeds of compression waves in the coupling prism 18 and in the plate 12 respectively. The transducer 16 in the transmitter 14 is connected to an electronic pulse generator 20, while the transducer 16 in the receiver is connected via an amplifier 22 to a signal analysis and display unit 24, which may for example include an oscilloscope.

When the transducer 16 in the transmitter 14 is energised it generates a pulse of compression waves in the coupling prism 18. This generates a pulse of lateral waves 26 propagating adjacent to the surface of the plate 12, and also generates a pulse of shear waves 28 propagating in a direction $\theta_c$ from the normal, where $$\theta_c = \sin^{-1}(C_s/C_p)$$

where $C_s$ is the speed of shear waves in the plate 12. The angle $\theta_c$ may be referred to as the shear/compression critical angle, and for steel with $C_p$=5.9 km/s and $C_s$ 3.2 km/s the critical angle $\theta_c$ is 32.8°. When this pulse of shear waves 28 reaches the other surface of the plate 12 not only does it reflect back as shear waves 30, but it also generates a pulse of lateral waves 32 propagating adjacent to that surface. Thus lateral waves 26 and 32 propagate along both surfaces of the plate 12; furthermore, at all places where a lateral wave 26 or 32 propagates, a head wave or shear wave is also generated propagating parallel to the shear waves 28 or 30.

At the receiver 15 the lateral waves 26 on the top surface, and the head waves transmitted parallel to the waves 30 by the lateral waves 32 at the rear surface, both generate compression waves in the coupling prism 18, and so are coupled to the transducer 16. The display 24 can therefore be expected to show a series of peaks, for each pulse generated by the transmitter 14, the first peak corresponding to waves travelling as a lateral wave 26 the entire distance between the transmitter 14 and the receiver 15, and subsequent peaks corresponding to waves which have crossed the thickness of the plate 12 as head waves 28, 30 two, four, six etc. times respectively, and travelled the rest of the way as lateral waves 26 or 32 on one or other of the surfaces. Each received peak corresponds to an infinite number of different such ray paths through the plate 12; all ray paths which involve the same number of crossings of the plate 12 lead to the same arrival time at the receiver 15. The locations where the crossings take place do not affect the propagation time.

In FIG. 1 the wave paths are indicated by rays, but it will be appreciated that the transmitter 14 will in fact generate a beam of finite width which will slightly diverge. In any situation where the phase of the wave varies over the width of a beam, if the beam is reflected from a surface there is a skip along the surface, that is to say the reflected wave experiences a small translation along the surface at each reflection. The size of this translation depends upon the variation in the phase change on reflection with the angle of incidence; if the surface is adjacent to a liquid such a translation will occur at any angle (Bertoni et al. J. Appl. Phys. 1973, 2, p.157), whereas if the surface is dry it only occurs above the shear-compression critical angle $\theta_c$. In the vicinity of the critical angle $\theta_c$ the translation can be half a wavelength or more (Harker, 1988, Elastic Waves in Solids (Adam Hilger) p.47).

It thus follows that the maximum number, n, of double crossings of the plate 12 is given by:

$$n \leq \frac{R}{2h \tan\theta_c + 2d}$$

where R is the distance between the transmitter 14 and the receiver 15, h is the thickness of the plate 12, and d is the skip or translation at reflection.

A further consequence of the finite beam widths, is that the transmitter 14 will also generate bulk compression waves in the plate 12 propagating at large angles from the normal, but less than 90°. These will also reflect from the surfaces one or more times before being received by the receiver 15. Equally, bulk compression waves may be generated when the initially-produced shear waves 28 hit the rear surface, which then travel to the receiver 15, as the shear wave beam 28 is also slightly divergent. These compression waves consequently produce a different series of peaks, which arrive just after the lateral wave 26.

Figure 2:
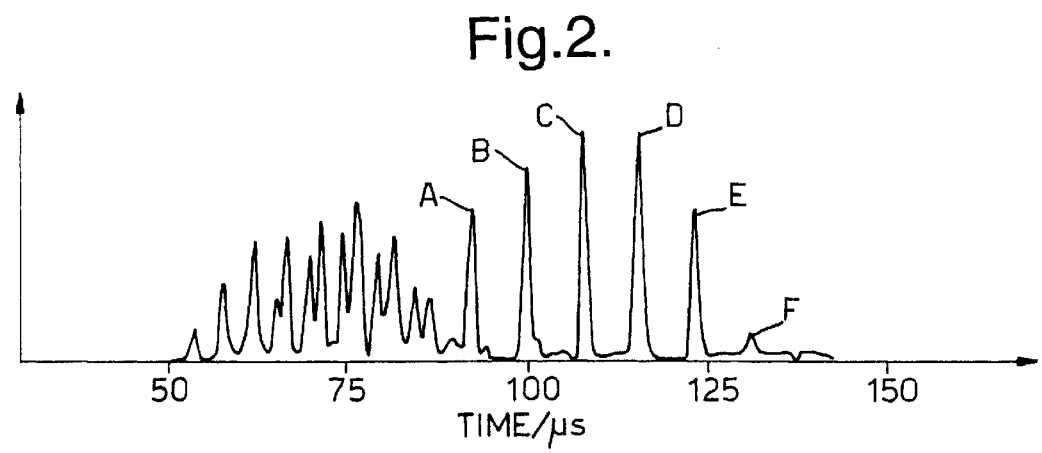
FIG. 2 shows graphically a series of ultrasonic peaks received in operation of the apparatus of FIG. 1.

Referring now to FIG. 2 there is shown the peak series shown on the display 24, with the apparatus 10 used on the plate 12 as described. The transmitter 14 and receiver 15 are 260 mm apart; the speed of compression waves $C_p$ is 5.9 mm/μs, so the first peak should be received at a time 44 μs after the transmission of a pulse. Between then and about 90 μs there appear to be two sets of received peaks. From 90 μs to 135 μs there is the single series of received peaks marked A–F at about 8 μs intervals, due to different numbers of double crossings of the plate 12 by head waves. The numbers of double crossings involved in each of these peaks appear to be, respectively, six, seven, eight, nine, ten, and eleven. If the skip distance d is taken as equal to the wavelength of shear waves at 2.25 MHz, these numbers agree with the equation given above, i.e.

$$n \leq \frac{260}{2 \times 15 \times \tan 32.8° + 2.8} = 11$$

Figure 3:
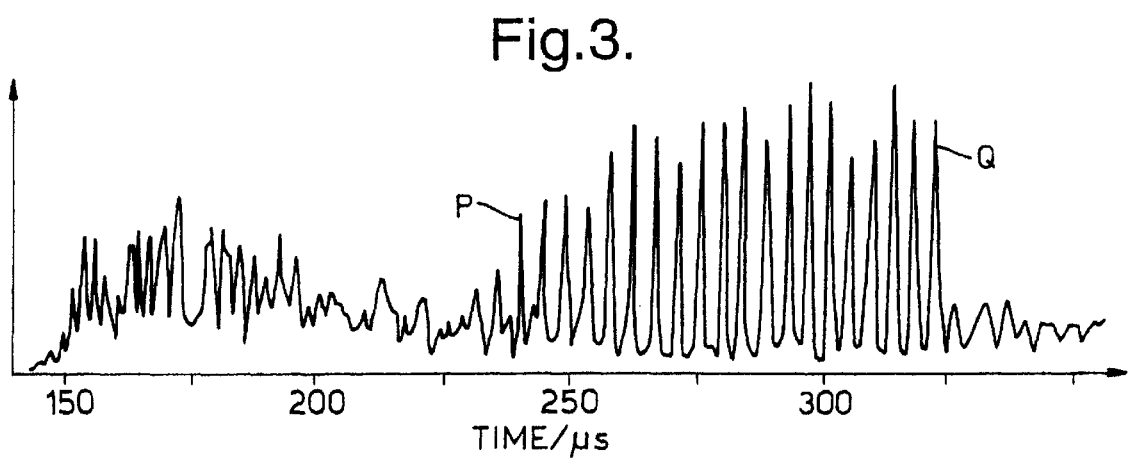
FIG. 3 shows graphically a series of ultrasonic peaks received in use of the apparatus of FIG. 1 to inspect a steel pipe wall.

Referring now to FIG. 3 there is shown the peak series shown in the display 24 when the apparatus 10 is instead used on a steel pipe of diameter 254 mm and wall thickness 9 mm, with the transmitter 14 and receiver 15 coupled to the pipe 720 mm apart along its length. In this case the number of received peaks is considerably larger both because the wall is thinner than the plate 12, and because the propagation distance R is larger. The first peak would be expected at a time of about 120 μs. Up to about 230 μs there are many peaks, and their spacing is not regular, whereas between 230 μs and 330 μs there is a single series of received peaks at intervals of about 4.2 μs. It may be estimated that the peaks marked P and Q correspond respectively to numbers of double crossings of the pipe wall of about twenty six and forty five respectively. With the assumptions made previously as to the value of the skip distance d, the predicted value of the maximum number of double crossings is $n \leq 50$.

If the object under investigation has a defect, such as a crack, the pattern of received peaks can be expected to change. For example a crack extending part way through the thickness of the plate 12 will obstruct those shear waves that would have propagated through that part of the plate; these waves will instead be reflected back. The reflected waves may be detected by means of a second amplifier and signal analysis and display unit connected to the transducer 16 of the transmitter 14. A series of reflected peaks can be expected to be received at the transmitter 14 due to the defect, and the time at which the first is detected may be used to determine the distance to the defect. The series of peaks received at the receiver 15 will also be changed, one or more of the peaks being of decreased amplitude or not received at all, depending on the size of the crack. It will be appreciated that substantially the entire volume of the object between the transducers is inspected; however if the opposed major surfaces differ significantly in curvature there may be some intervening parts of the object which are not inspected. Where the object is a pipe, for example, then inspection of the entire volume of the pipe wall can be expected as long as the wall thickness is less than about 8% of the diameter.

Figure 4A:
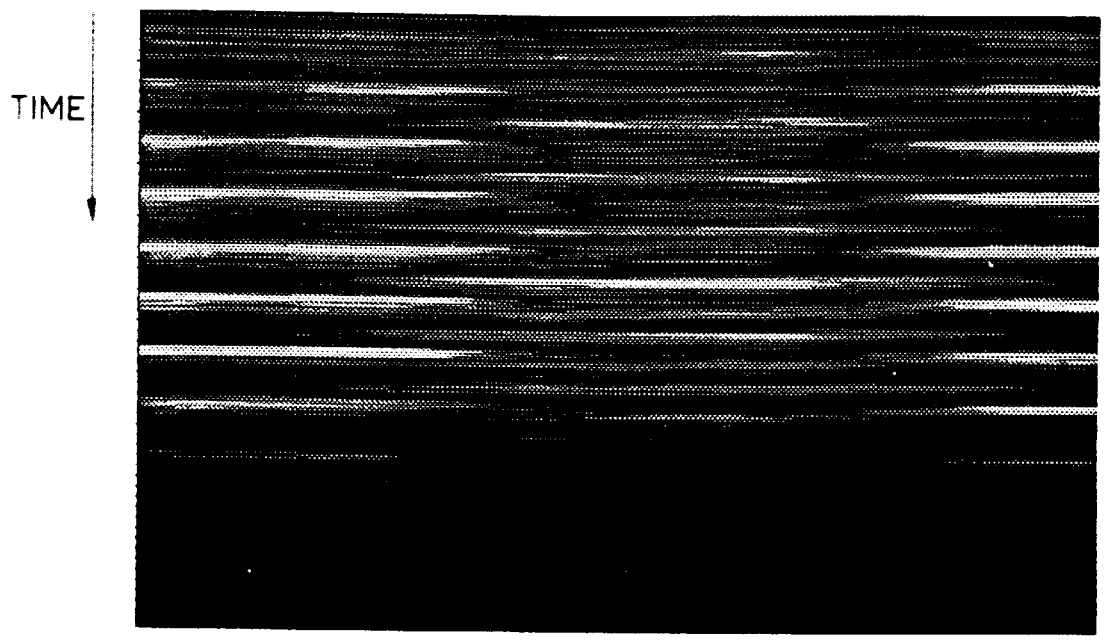
FIGS. 4a and b show B-scans obtained with the apparatus of FIG. 1 inspecting a steel pipe wall with a notch.
Figure 4B:
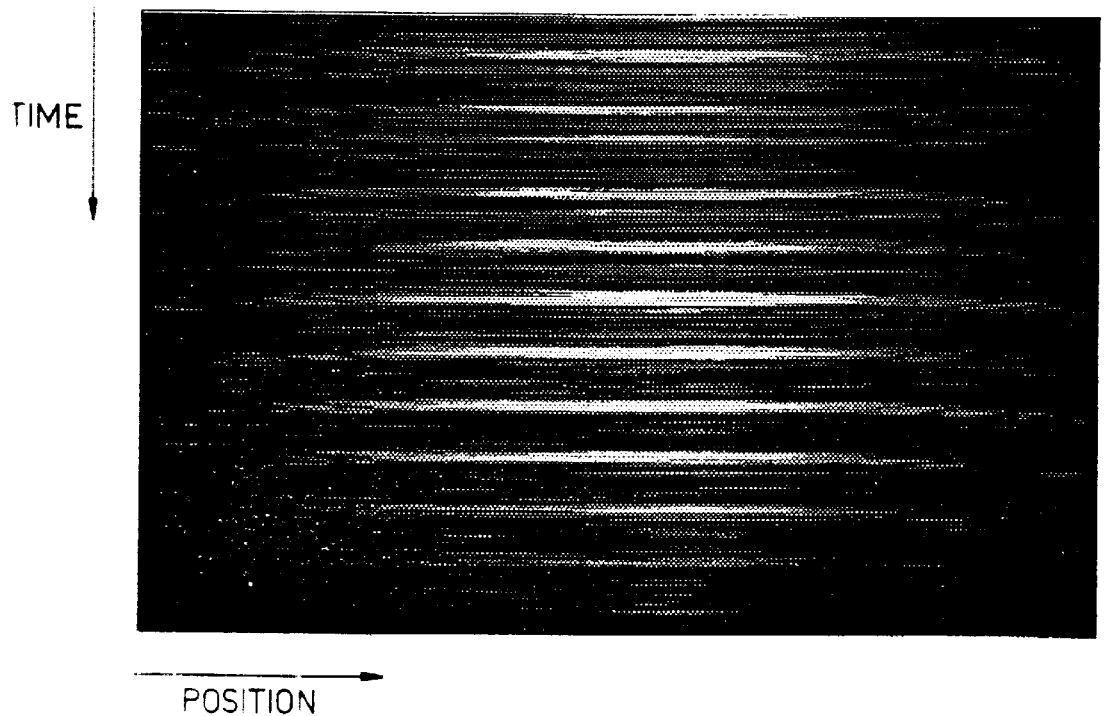

Referring now to FIGS. 4a and b there are shown B-scans obtained using the apparatus 10 for inspection of a steel pipe of diameter 305 mm and wall thickness 11 mm, the apparatus being modified by also including an amplifier 22 and a signal analysis and display unit 24 connected to the transmitter 14, so that reflected signals can also be observed. To represent the effect of a defect, a rectangular notch or recess had been machined in the inner surface, 50 mm wide and 20 mm long (along the line between the transmitter 14 and the receiver 15) and 4 mm deep. The transmitter 14 and the receiver 15 were 260 mm apart, and were scanned along the pipe starting well to one side of the notch, crossing the region with the notch, and ending well to the other side of the notch. The location of the notch is indicated next to each B-scan by a line N. Each B-scan represents the intensity of the received ultrasonic signals by the lightness (i.e. black=no signal; white=maximum signal), the axes representing the position along the pipe during the scan, and the time of receipt of the ultrasonic signal. FIG. 4a shows the signals received by the receiver 15, i.e. the "transmitted signal B-scan" whereas FIG. 4b shows the reflected signals received by the transmitter 14, i.e. the "reflected signal B-scan".

It will be observed that before the scan reaches the notch, there are no reflected signals (see FIG. 4b), but the transmitted signal B-scan has about seven well defined peaks, equally spaced in time (the time axis starts just before the first of the well-defined peaks, analogous to just before peak A in FIG. 2 or just before peak P in FIG. 3). As the scan traverses the notch the transmitted signal B-scan changes, the initial peaks fading away and new peaks appearing at different times. At the same position in the scan a series of peaks appears in the reflected signal B-scan. When the notch has been passed, both B-scans return to the initial features, with no reflected signals, and with about seven well defined peaks in the transmitted signal B-scan. Evidently either of these b-scans could be used to detect the presence of such a notch.

What is claimed is:

1. A method for inspecting an object (12) with two opposed substantially parallel major surfaces, the method comprising coupling a transmitter ultrasonic transducer (14) to one of the major surfaces of the object (12) so as to generate shear waves (28) in the object (12) propagating in a direction inclined from the normal to the surface at an angle substantially equal to the shear-compression critical angle ($\theta_c$); coupling a receiver ultrasonic transducer (15) to one of the major surfaces of the object (12) so as to detect shear waves (30) incident at an angle of incidence equal to the shear-compression critical angle ($\theta_c$); energising the transmitter transducer (14) to generate at least one pulse of ultrasound; and detecting by means of the receiver transducer (15) a series of ultrasonic peaks corresponding to each generated pulse, the series of peaks being due to ultrasonic waves which have propagated through the object (12) partly as lateral waves (26,32) on the major surfaces and partly as head waves (28,30) traversing the object (12) between the major surfaces.

2. A method as claimed in claim 1 wherein the transmitter transducer and the receiver transducer are the same transducer.

3. A method as claimed in claim 1 wherein the transmitter transducer (14) is separate from the receiver transducer (15) and is spaced apart from it.

4. A method as claimed in claim 3 wherein the transducers (14,15) are more than 0.25 m apart from each other.

5. A method as claimed in claim 1 wherein the detected series of peaks is analysed to provide information about the thickness of the object, or localised variations in thickness.

6. A method as claimed in claim 1 wherein the detected series of peaks is analysed to detect any defects, flaws or cracks in the object (12).

7. A method as claimed in claim 1 wherein signals received between successive peaks in the series are examined.

* * * * *